(12) United States Patent
Wagealla et al.

(10) Patent No.: US 12,599,569 B1
(45) Date of Patent: Apr. 14, 2026

(54) ENCAPSULATED RESVERATROL (RSV) NANOPARTICLES

(71) Applicant: KING SAUD UNIVERSITY, Riyadh (SA)

(72) Inventors: Mai Abdelrahman Elobeid Wagealla, Riyadh (SA); Atheer Mohammed Asiri, Riyadh (SA); Promy Virk, Riyadh (SA); Manal Ahmed Gasmelseed Awad, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/004,832

(22) Filed: Dec. 30, 2024

(51) Int. Cl.
| | |
|---|---|
| *A61K 9/50* | (2006.01) |
| *A61K 31/05* | (2006.01) |

(52) U.S. Cl.
CPC .......... *A61K 9/5036* (2013.01); *A61K 9/5026* (2013.01); *A61K 31/05* (2013.01)

(58) Field of Classification Search
CPC ..... A61K 9/5036; A61K 9/5026; A61K 31/05
See application file for complete search history.

(56) References Cited

U.S. PATENT DOCUMENTS

| | | | |
|---|---|---|---|
| 10,882,012 B2 | 1/2021 | Dang et al. | |
| 2012/0219604 A1* | 8/2012 | Kim ...................... | A61K 36/16 424/400 |
| 2014/0309294 A1* | 10/2014 | Erfurt ................... | A23L 33/105 426/321 |

FOREIGN PATENT DOCUMENTS

| | | |
|---|---|---|
| CN | 201657749 U | 12/2010 |
| CN | 106234914 A | 12/2016 |
| CN | 111329063 A | 6/2020 |

OTHER PUBLICATIONS

Liu et al., "Treatment with ultrasound improves the encapsulation efficiency of resveratrol in zein-gum Arabic complex coacervates", Food Science and Technology, 153 (2022), 112331. (Year: 2022).*

Alshamsan, "Nanoprecipitation is more efficient than emulsion solvent evaporation method to encapsulate cucurbitacin I in PLGA nanoparticles," Saudi Pharmaceutical Journal, vol. 22, Issue 3, Jul. 2014, pp. 219-222.

Wu, et al., "Fabrication and characterization of resveratrol-loaded gliadin nanoparticles stabilized by gum Arabic and chitosan hydro-chloride," LWT, vol. 129, Jul. 2020.

Thipe, et al., "Development of resveratrol-conjugated gold nanoparticles: interrelationship of increased resveratrol corona on anti-tumor efficacy against breast, pancreatic and prostate cancers," International Journal of Nanomedicine, vol. 14, pp. 4413-4428, Jun. 18, 2019.

* cited by examiner

*Primary Examiner* — Jianfeng Song
(74) *Attorney, Agent, or Firm* — Nath, Goldberg & Meyer; Joshua B. Goldberg

(57) ABSTRACT

Encapsulated resveratrol (RSV) nanoparticles having a resveratrol core, a gum arabic shell, and a polyvinyl alcohol coating over the gum arabic shell. In an embodiment, an RSV:gum arabic:polyvinyl alcohol (PVA) ratio in the encapsulated nanoparticles is about 1:5:5 (w/w/w). The encapsulated RSV nanoparticles can have an average size ranging from about 195 nm to about 210 nm.

11 Claims, 6 Drawing Sheets

|  | Size (d.nm): | % Intensity: | St Dev (d.nm): |
|---|---|---|---|
| Z-Average (d.nm): 207.8 | Peak 1: 229.5 | 98.4 | 81.62 |
| Pdt: 0.222 | Peak 2: 5210 | 1.6 | 468.5 |
| Intercept: 0.949 | Peak 3: 0.000 | 0.0 | 0.000 |
| Result quality : Good | | | |
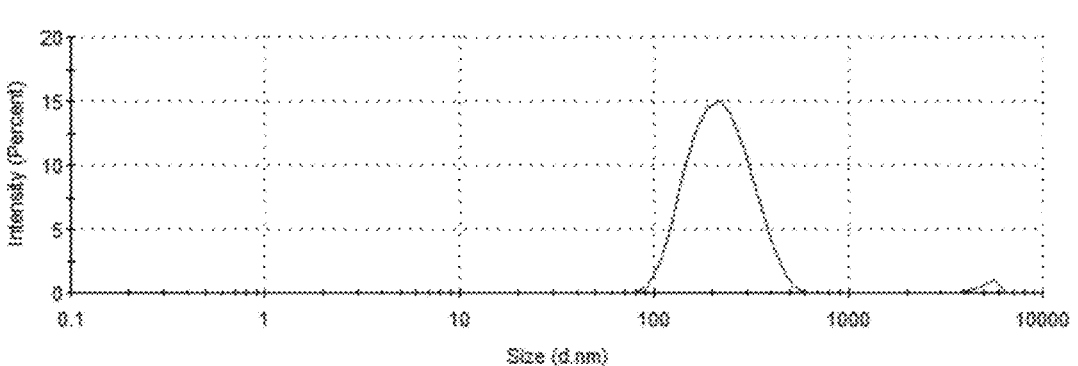
Size Distribution by Intensity
FIG. 1

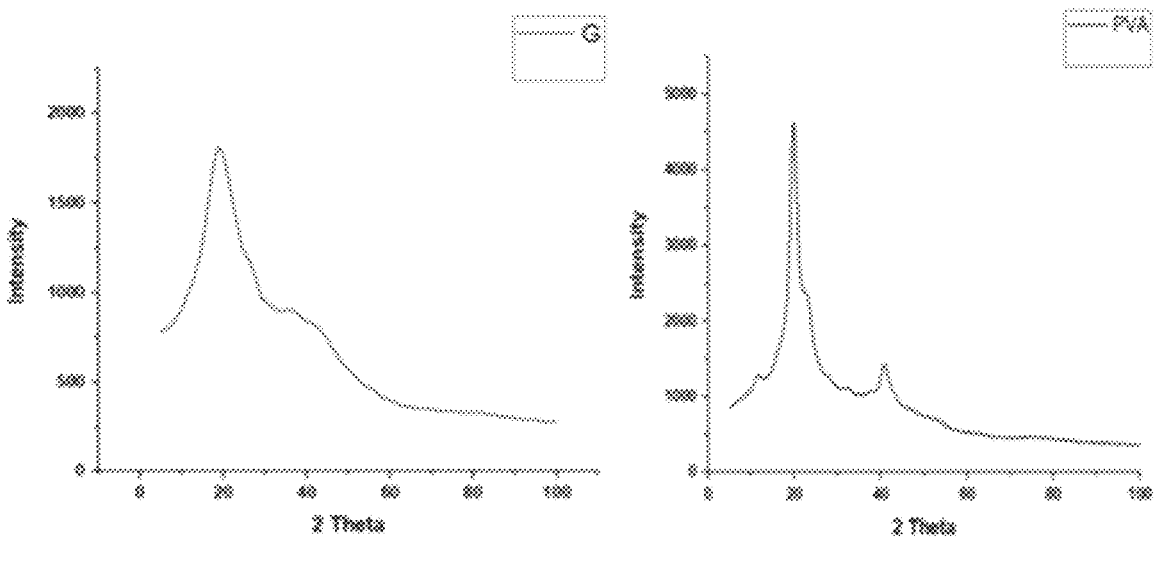
FIG. 2A                    FIG. 2B
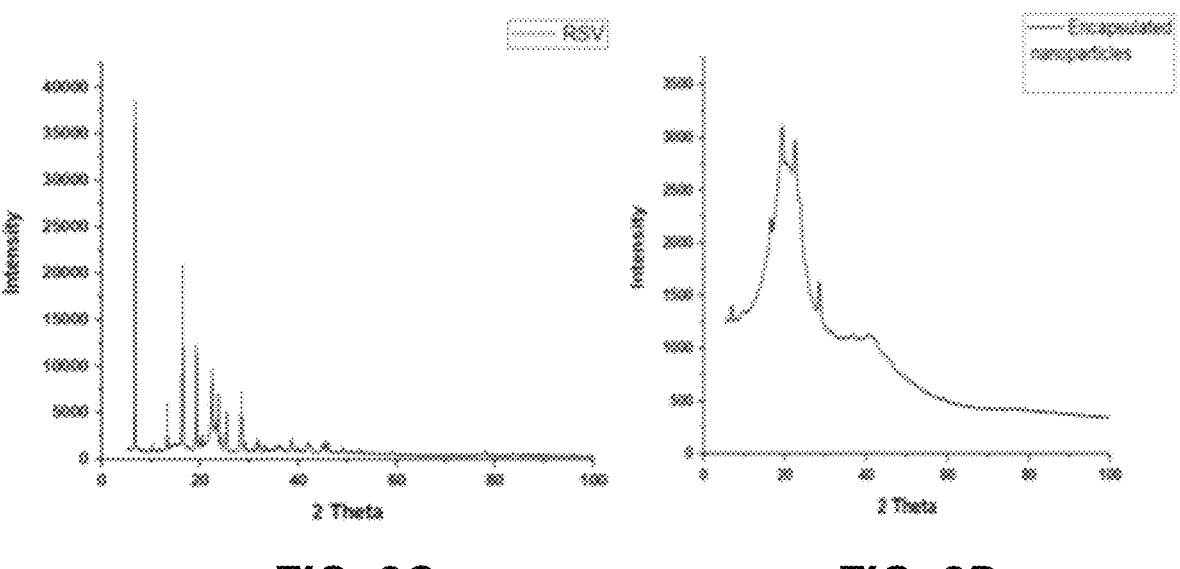
FIG. 2C                    FIG. 2D

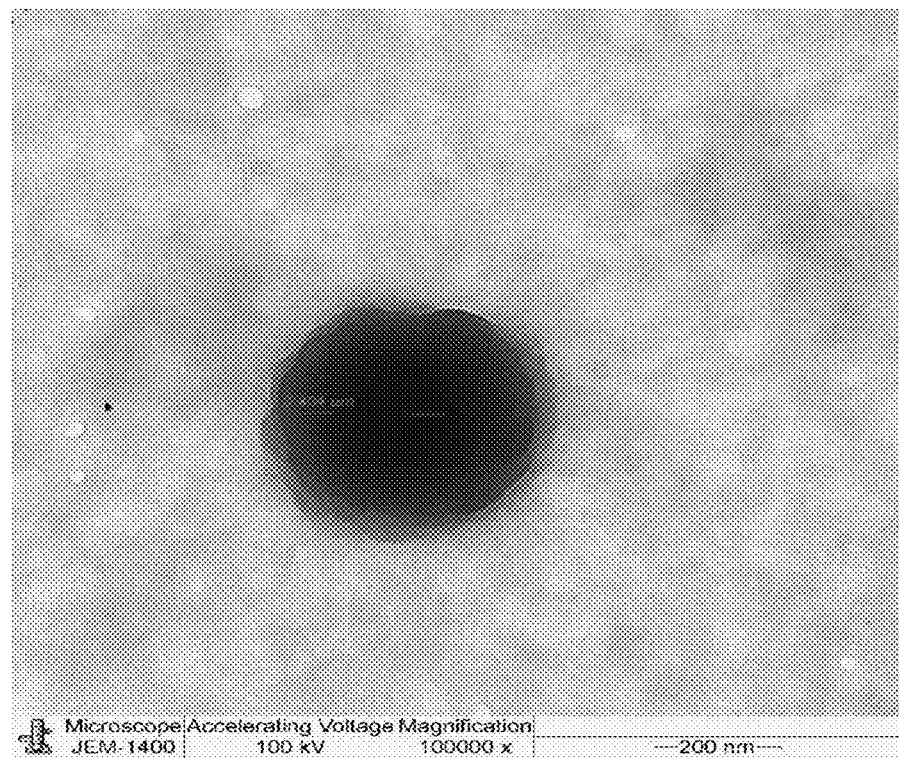
*FIG. 3B*
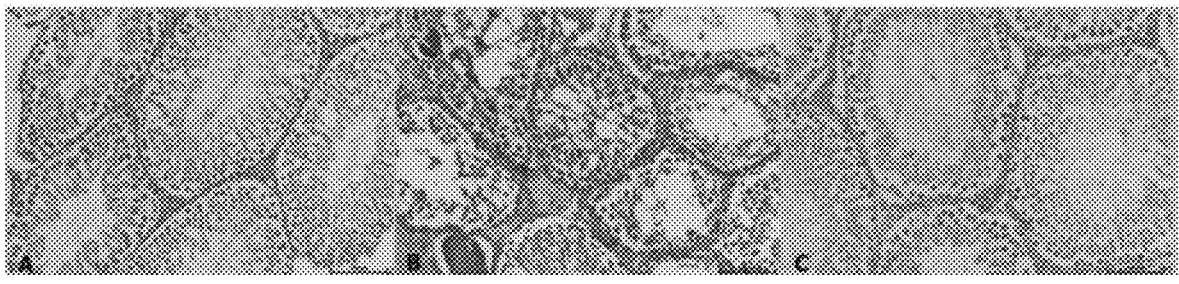
*FIG. 4A*                    *FIG. 4B*                    *FIG. 4C*

ENCAPSULATED RESVERATROL (RSV) NANOPARTICLES

BACKGROUND

1. Field

The present disclosure relates to encapsulated resveratrol (RSV) nanoparticles and, particularly, to encapsulated resveratrol (RSV) nanoparticles having a resveratrol core, a gum arabic shell over the resveratrol core, and a polyvinyl alcohol coating over the gum arabic shell.

2. Description of the Related Art

Resveratrol (RSV) is a polyphenolic nutraceutical that exhibits a wide range of curative properties, including improving the therapeutic outcome in patients suffering from diabetes mellitus, obesity, colorectal cancer, breast cancer, multiple myeloma, metabolic syndrome, hypertension, Alzheimer's disease, stroke, cardiovascular diseases, kidney diseases, inflammatory diseases, and rhinopharyngitis.

Recently, RSV has gained a considerable amount of attention from researchers as evidenced by accumulated studies related to pre-clinal trials, clinical trials, and rodent models (Ahmadi and Ebrahimzadeh, 2020; Farkhondeh et al., 2020, Virk et al., 2020). Resveratrol, a type of phytoalexin produced in response to fungal attack, bacterial attack, or UV radiation exposure, is usually found in red grape skins, red wine, purple grape juice, mulberries, and in smaller amounts in peanuts (Ahmadi and Ebrahimzadeh, 2020).

Nanotechnology is increasingly being utilized to devise novel formulations for oral delivery of nutraceuticals. Combining phytomedicine with nanotechnology has been widely proposed and considered as a revolutionary approach, owing to several advantages provided by nano-formulated herbal medicines, including enhancing bioavailability of various plant extracts, eliminating side effects, and directing the active component of the plant extracts at a sufficient concentration to the target site inside the organism's body.

Thus, resveratrol nanoparticles solving the aforementioned problems are desired.

SUMMARY

The present subject matter relates to encapsulated resveratrol (RSV) nanoparticles have a resveratrol core, a gum arabic shell, and a polyvinyl alcohol coating over the gum arabic shell. The encapsulated RSV nanoparticles can have an average size ranging from about 195 nm to about 210 nm, for example, about 207.8 nm. The encapsulated RSV nanoparticles can have a polydispersity index (PDI) ranging from about 0.195 to about 0.225, e.g., about 0.222, which indicates the mono-dispersity of the nanoparticles. The encapsulated RSV nanoparticles can be spherical. The encapsulated RSV nanoparticles can be used to treat a wide array of pathologies, including "diseases of civilization," such as Alzheimer's disease, atherosclerosis, cancer, chronic liver disease, Type 2 diabetes, heart disease, hypertension, and stroke.

According to an embodiment, a method of preparing encapsulated resveratrol (RSV) nanoparticles can include spraying a resveratrol extract into boiling water to produce a first mixture; combining gum arabic with the first mixture to provide a second mixture; dissolving the second mixture in alcohol to provide a third mixture; injecting the third mixture into polyvinyl alcohol (PVA) to provide a final solution; and homogenizing the final solution to provide the encapsulated nanoparticles.

According to an embodiment, encapsulated resveratrol (RSV) nanoparticles can include a resveratrol core, a gum arabic shell, and a polyvinyl alcohol coating over the gum arabic shell. An RSV:gum arabic:polyvinyl alcohol (PVA) ratio in the encapsulated nanoparticles can be about 1:5:5 (w/w/w).

These and other features of the present subject matter will become readily apparent upon further review of the following specification.

BRIEF DESCRIPTION OF DRAWINGS

FIG. 1 shows the size distribution of the encapsulated nanoparticles described herein.

FIGS. 2A-2D shows the X-ray Diffraction (XRD) spectra of (FIG. 2A) Gum arabic (G), (FIG. 2B) PVA, (FIG. 2C) RSV, and (FIG. 2D) GPVA-coated RSV (encapsulated nanoparticles).

FIGS. 3A-3B are Transmission Electron Microscopy images (TEM) of the encapsulated nanoparticles of RSV.

FIGS. 4A-4F are images showing expression of apoptosis-related factor: Bax (bar=100 µm) in (FIG. 4A) control group: negative Bax immune reactivity which indicates no apoptotic cells can be observed; (FIG. 4B) 0.1 mg/kg ZEA: the seminiferous tubules indicated large positive reaction revealing intense Bax immunoreactivity (arrows), and apoptosis was observed; (FIG. 4C) 0.1 mg/kg ZEA+10 mg/kg RSV; (FIG. 4D) 0.1 mg/kg ZEA+10 mg/kg RSV NPs, showing moderate to low Bax immunoreactivity (arrows) the apoptosis rate of spermatogenic cells was low, typical apoptotic cells were few, and some of the particles were weakly positive; (FIG. 4E) 10 mg/kg RSV; and (FIG. 4F) 10 mg/kg RSV Nps negative Bax Immunoreactivity which indicates no apoptotic cells can be observed.

FIGS. 5A-5F show expression of: apoptosis-related factor Bcl-2 (bar=100 µm) in (FIG. 5A) control group: testes showing an intense Bcl-2 immunoreactivity (no apoptotic cells); (FIG. 5B) 0.1 mg/kg ZEA: revealed weak and almost no Bcl-2 immunoreactivity; (FIG. 5C) 0.1 mg/kg ZEA+10 mg RSV: displaying moderate Bvl-2 immunoreactivity; (FIG. 5D) 0.1 mg/kg ZEA+10 mg/kg RSV NPs: showing an intense Bcl-2 immunoreactivity; (FIG. 5E) 10 mg/kg RSV; and (FIG. 5F) 10 mg/kg RSV NPs: showing an intense Bcl-2 immunoreactivity.

DETAILED DESCRIPTION OF THE PREFERRED EMBODIMENTS

Figure 3A:
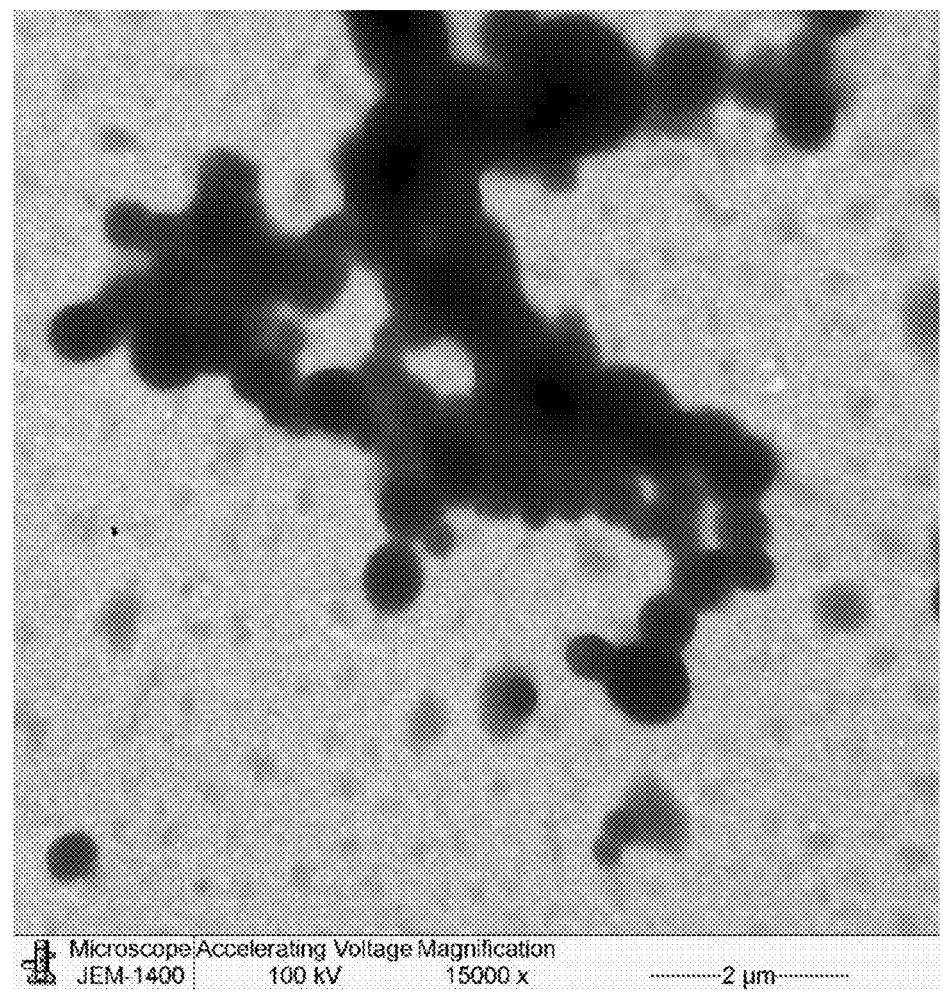

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to encapsulated resveratrol (RSV) nanoparticles (also referred to herein as RSV NPs) having a resveratrol core, a gum arabic shell, and a polyvinyl alcohol coating over the gum arabic shell. In an embodiment, an RSV:Gum arabic:Polyvinyl alcohol (PVA) ratio in the encapsulated nanoparticles can be about 1:5:5 (w/w/w). The encapsulated RSV nanoparticles can have an average size ranging from about 195 nm to about 210 nm, for example, about 207.8 nm. The encapsulated RSV nanoparticles can have a polydispersity index (PDI) ranging from about 0.195 to about 0.225, e.g., about 0.222, which indicates the mono-dispersity of the nanoparticles. According to an embodiment, the encapsulated RSV nanoparticles can be spherical in shape.

According to an embodiment, the encapsulated RSV nanoparticles can be used to treat a wide array of pathologies, including "diseases of civilization," such as Alzheimer's disease, atherosclerosis, cancer, chronic liver disease, Type 2 diabetes, heart disease, hypertension, and stroke.

According to an embodiment, the encapsulated RSV nanoparticles can be administered to a patient for increasing Bcl-2 immunoreactivity. As is generally known, the Bcl-2 family of proteins is the key regulator of apoptosis. Abnormalities in the function of Bcl-2 proteins have been implicated in many diseases including, cancer, neurodegenerative disorders, ischemia, and autoimmune diseases.

According to an embodiment, a method of treating a disease selected from the group consisting of cancer, a neurodegenerative disease, ischemia, and an autoimmune disease can include administering the encapsulated RSV nanoparticles to a patient in need thereof. In an embodiment, the neurodegenerative disease can be Alzheimer's disease. In an embodiment, the cancer can be breast cancer.

According to an embodiment, the encapsulated RSV nanoparticles can be administered to a patient for increasing sex hormone-binding globulin (SHBG). Sex hormone-binding globulin (SHBG) is produced and secreted by the human liver into the blood. Low plasma SHBG levels are associated with obesity and the metabolic syndrome predicting risk for type 2 diabetes and cardiovascular disease.

According to an embodiment, a method of treating a disease selected from the group consisting of obesity, type-2 diabetes, and cardiovascular disease as described herein can include administering a therapeutically effective amount of the presently described encapsulated nanoparticles to a patient in need thereof.

As described herein, the therapeutic efficacy of the encapsulated RSV nanoparticles can be evaluated based on immunohistochemical assessment of apoptosis-related factors (Bax and Bcl-2) in the testis and the gene expression of constitutive androstane receptor (CAR), a well-known xenobiotic-sensing nuclear receptor in the liver, of rats exposed to a fungal mycotoxin, zearalenone (ZEA). The encapsulated RSV nanoparticles reversed the toxic effects of the mycotoxin, as reflected by intense Bcl-2 immunoreactivity and negligible Bax immunoreactivity. Further, the expression of the CAR gene was enhanced by treatment with the present RSV nanoparticles.

In a further embodiment, the present subject matter relates to a method of making encapsulated RSV nanoparticles including spraying a resveratrol extract into boiling water to produce a first mixture. In an embodiment, the resveratrol extract can be sprayed dropwise into boiling water under ultrasonic conditions. In an embodiment, the resveratrol extract can be sprayed at a flow rate ranging from about 0.1 ml/min to about 0.5 ml/min, e.g., about 0.2 ml/min, or 0.2 ml/min, for a period of time ranging from about 1 min to about 5 min, e.g., about 2 min, or 2 min, under ultrasonic conditions. The ultrasonic conditions can include, for example, an ultrasonic power ranging from about 550 W to about 800 W, e.g., about 750 W, or 750 W. and a frequency of about 10 kHz to about 30 kHz, e.g., about 20 kHz, or 20 KHz.

According to an embodiment, gum arabic can be combined with the first mixture to provide a second mixture and the second mixture can be dissolved in a first alcohol, e.g., ethanol, to provide a third mixture. The third mixture can be injected into a second alcohol, e.g., polyvinyl alcohol (PVA), and the resulting final solution can be homogenized to provide the presently described encapsulated RSV nanoparticles. In an embodiment, an RSV:Gum arabic:(polyvinyl alcohol) PVA ratio in the final solution can be about 1:5:5; w/w/w, or 1:5:5, w/w/w.

According to one embodiment, an amount of about 100 mg of RSV and an appropriate amount of gum arabic can be dissolved in about 50 ml of ethanol to provide an internal organic phase solution. The internal organic phase solution can be injected into about 100 ml of an external aqueous solution including PVA, and the resulting solution can be homogenized at about 22,000 rpm for about 15 minutes to form the encapsulated RSV nanoparticles.

The present subject matter further relates to a pharmaceutical composition, which comprises the encapsulated RSV nanoparticles as described herein together with at least one pharmaceutically acceptable carrier.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compositions are typically administered at a therapeutically or pharmaceutically effective dosage, e.g., a dosage sufficient to provide treatment for a disease selected from the group consisting of Alzheimer's disease, atherosclerosis, cancer, chronic liver disease, Type 2 diabetes, heart disease, hypertension, and stroke. Administration of the compounds or pharmaceutical compositions thereof can be by any method that delivers the compositions systemically and/or locally. These methods include oral routes, parenteral routes, intraduodenal routes, and the like.

While human dosage levels have yet to be optimized for the present compositions, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compositions for treatment of a disease, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compositions can also be administered in sustained or controlled release dosage forms, including depot injections, osmotic pumps, pills, transdermal (including electrotransport) patches, and the like, for the prolonged administration of the present nanoparticles at a predetermined rate, preferably in unit dosage forms suitable for single administration of precise dosages.

The present compositions may also be administered as foods for humans or animals, including medical foods, functional foods, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present nanoparticles, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the present nanoparticles, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. the encapsulated RSV nanoparticles as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410, 545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the present nanoparticles in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of the present nanoparticles contained in such parenteral compositions is highly dependent on the specific nature thereof, as well as the activity of the compound and the needs of the subject. However, percentages of the present nanoparticles of 0.01% to 10% in solution are employable and will be higher if the composition is a solid which will be subsequently diluted to the above percentages. The composition may comprise 0.2% to 2% of the present nanoparticles in solution.

Nasal solutions of the present nanoparticles alone or in combination with other pharmaceutically acceptable excipients can also be administered.

Formulations of the present nanoparticles may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present nanoparticles have valuable pharmaceutical properties, which make them commercially utilizable. Accordingly, the present subject matter further relates to use of the present pharmaceutical composition for the treatment of diseases such as Alzheimer's disease, atherosclerosis, cancer, chronic liver disease, Type 2 diabetes, heart disease, hypertension, and stroke.

The present subject matter further relates to a method of treating or preventing a disease comprising administering to a patient in need thereof a therapeutically effective amount of the pharmaceutical composition described herein.

In the above methods, the patient is preferably a mammal, more preferably a human.

The present teachings are illustrated by the following examples.

EXAMPLES

Example 1

Preparation of Encapsulated Nanoparticles

About 100 mg of resveratrol (RSV) was extracted in about 10 ml of methanol under constant stirring to produce a RSV extract. The RSV extract was sprayed into boiling water (30 ml) dropwise, with a flow rate of 0.2 ml/min, over 2 minutes, under ultrasonic conditions (ultrasonic power 750 W, frequency 20 kHz) to produce a mixture. The encapsulated nanoparticles were prepared with a ratio of RSV:Gum arabic:(Polyvinyl alcohol) PVA (1:5:5; w/w/w) using the nano precipitation technique (Shengfeng et al., 2018; Zili et al., 2005). An amount of 100 mg of RSV and the appropriate amount of gum Arabic was dissolved in 50 ml of ethanol. The internal organic phase solutions were quickly injected into the 100 ml external aqueous solution containing the appropriate amount of PVA, and then the solutions were homogenized at 22,000 rpm for 15 minutes. The methanol was completely removed.

Example 2

Characterization of the Nanoparticles

The dynamic light scattering (DLS) method was performed to determine the hydrodynamic size distribution and Polydispersity Index (Pdl) using a Zetasizer (HT Laser, ZEN3600 Malvern, UK). The obtained DLS curve (FIG. 1) shows the size distribution of synthesized encapsulated nanoparticles with an average size 207.8 nm and a polydispersity index (PDI) of 0.222, which indicates nanoparticles were mono-dispersed.

X-ray diffraction can determine crystalline structure or phase of crystal. Information about the solid-state properties of PVA-coated, Gum arabic-encapsulated RSV nanoparticles (GPVA-coated RSV nanoparticles) was obtained using X-ray diffraction. Diffraction peaks were detected for pure RSV at 2θ values ranging from 5° to 30° (FIG. 2), indicating that it was present in a highly crystalline structure. Diffraction peaks were observed for pure gum Arabic and PVA, indicating that it was not in a crystalline state. Interestingly, no diffraction peaks were observed when the encapsulated RSV nanoparticles were analyzed. This result suggests that confinement of RSV inside the GPVA (gum Arabic and PVA) shell inhibited its crystallization. This may be beneficial for certain delivery applications, since the bioavailability of amorphous forms of drugs has been shown to be higher than that of crystalline forms [R. Jog and D. J. Burgess, J. Pharm. Sci., 2017, 106, 39-65]

Example 3

Immunohistochemical Assessment of
Apoptosis-Related Factors (Bax and Bcl-2)

Figures 4D, 4E, 4F, 5A, 5B, 5C, 5D, 5E, 5F:
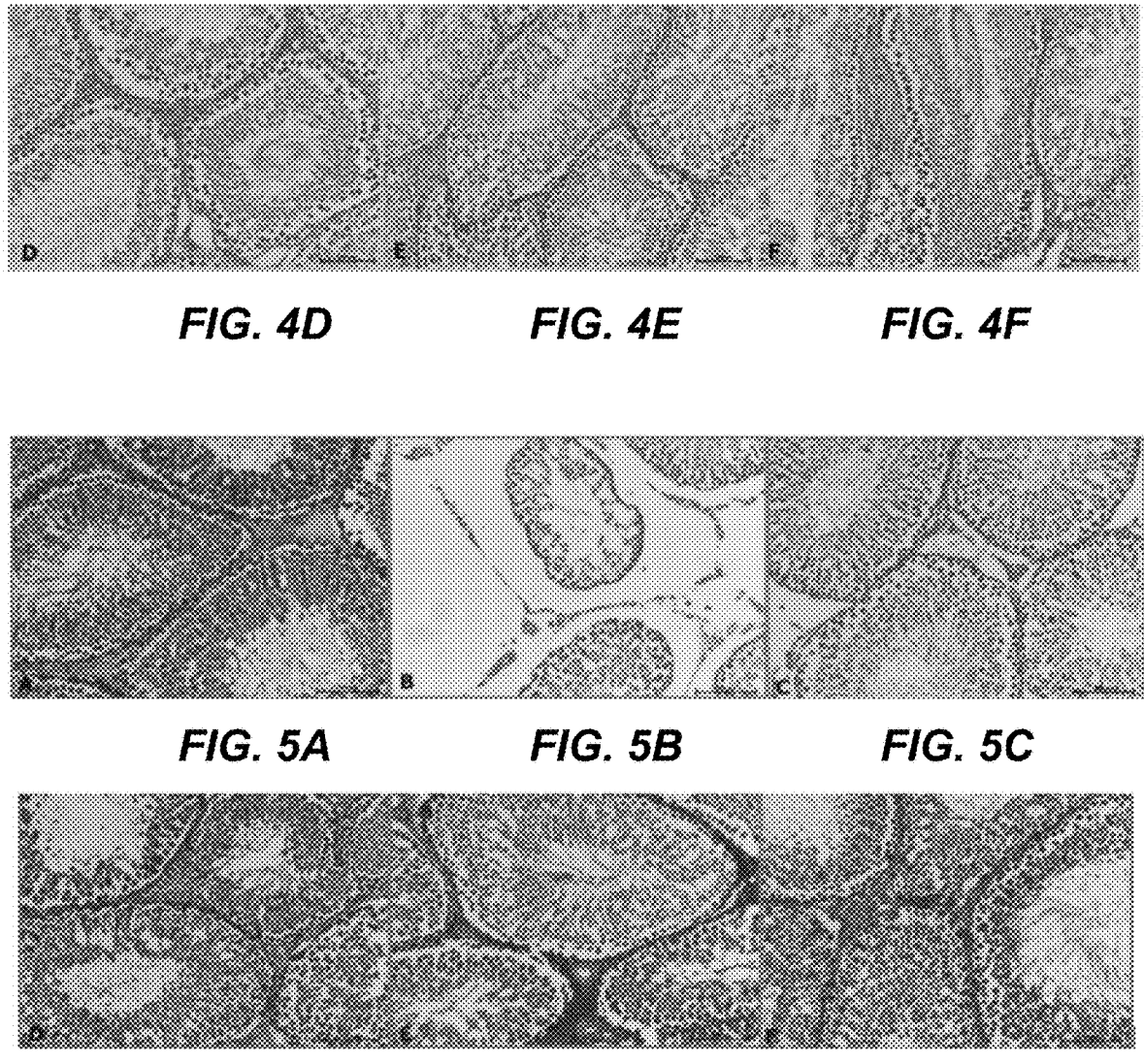

IHC assay was conducted to estimate the toxic impact of ZEA and the ameliorative effect of RSV and its nano-formulation on the expression of apoptosis-related factors (Bax and Bcl-2). Results of the IHC assay revealed that control testes tissue (treated with distilled water) have no Bax immunoreactivity (FIG. 4A). Testis tissue from the group treated with 0.1 mg/kg ZEA revealed intense Bax immunoreactivity (FIG. 4B). In contrast, the groups treated with 0.1 mg/kg ZEA+10 mg/kg RSV and 0.1 mg/kg ZEA+10 mg/kg RSV NPs showed moderate Bax immunoreactivity (FIGS. 4C and 4D). Almost no Bax immunoreactivity was detected in the groups treated with 10 mg/kg RSV or 10 mg/kg RSV NPs displayed, though some weakly positive reactions were observed in the spermatocytes (FIGS. 4E and 4F).

Testes sections stained immunohistochemically against Bcl-2 was noticeably higher (brown color) in control group that received distilled water (FIG. 5A), compared with the group that received 0.1 mg/kg of ZEA that have almost no Bcl-2 immunoreactivity (FIG. 5B). In case of the group that received 0.1 mg/kg ZEA+10 mg/kg RSV showed moderate Bcl-2 immunoreactivity in compared with the group that received 0.1 mg/kg ZEA+10 mg/kg RSV NPs that displayed an intense Bcl-2 immunoreactivity (FIGS. 5C and 5D). High Bcl-2 immunoreactivity was detected in the groups that received 10 mg/kg RSV or 10 mg/kg RSV NPs (FIGS. 5E and 5F).

The results on immunohistochemical assessment of apoptosis-related factors (Bax and Bcl-2) clearly show a marked curative effect of the RSVNPs on the expression of Bax and Bcl-2 factors in the sections of testis of rats exposed to the mycotoxin, ZEA and treated with the RSVNPs. Thus, the apoptosis induced by the mycotoxin was effectively reduced by the RSV, the effect of the RSVNPs was more pronounced than the bulk RSV. Several in vitro as well as a few in vivo studies have shown that resveratrol has multiple anti-cancer effects, protecting against both tumor initiation and cancer progression pathways as well as act as an antioxidant to prevent DNA damage that can lead to tumor formation (Carter et al., 2014).

It has been reported that resveratrol, a polyphenol enriched in red wine, acts specifically through the human

Figure 6:
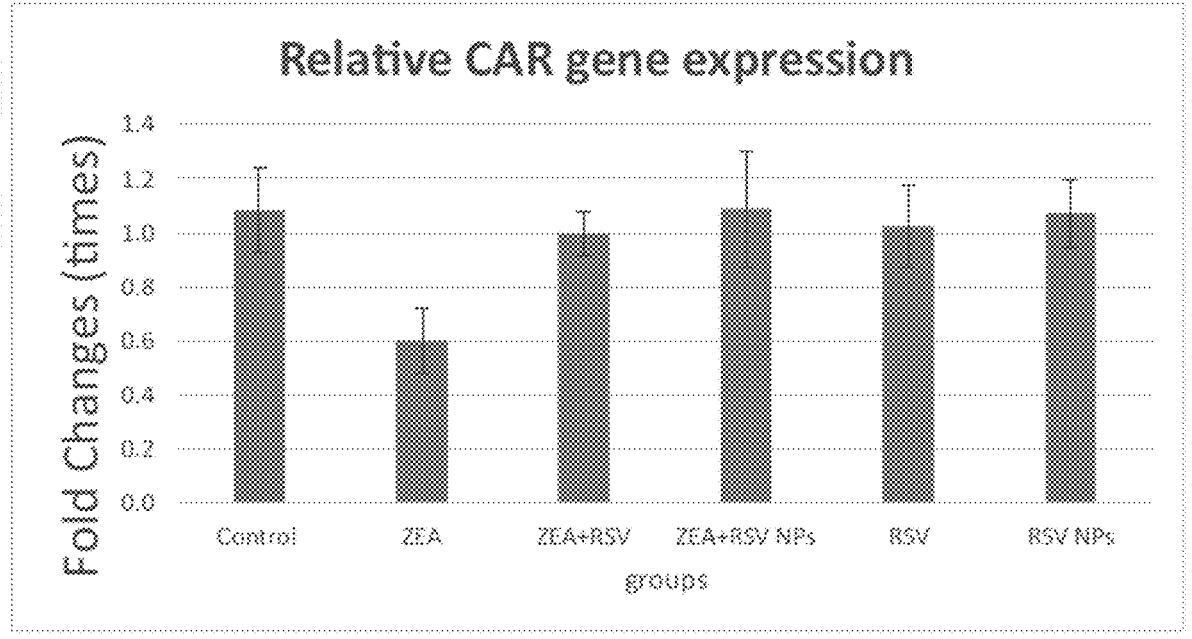
FIG. 6 is a graph showing relative CAR gene expression in rat liver exposed to the mycotoxin, ZEA and treated with encapsulated nanoparticles of resveratrol (RSVNPs) and resveratrol as bulk (RSV).

10 constitutive androstane receptor (CAR), a drug/xenobiotic detoxification gene regulator in the liver, to increase hepatic SHBG production (Saez-Lopez et al., 2017). This in in consensus with the results on CAR gene expression in the liver of rats exposed to ZEA and treated with RSVNPs which showed a marked increase in the relative expression of the gene (FIG. 6).

It is to be understood that the encapsulated RSV nanoparticles are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. Encapsulated resveratrol (RSV) nanoparticles, consisting of:
a resveratrol core;
a gum arabic shell over the resveratrol core; and
a polyvinyl alcohol coating over the gum arabic shell.

2. The encapsulated resveratrol (RSV) nanoparticles of claim 1, wherein an RSV:gum arabic:polyvinyl alcohol (PVA) ratio in the encapsulated nanoparticles is about 1:5:5 (w/w/w).

3. The encapsulated resveratrol (RSV) nanoparticles of claim 1, wherein the nanoparticles have an average size ranging from about 195 nm to about 210 nm.

4. The encapsulated resveratrol (RSV) nanoparticles of claim 3, wherein the encapsulated resveratrol (RSV) nanoparticles have an average size of about 207.8 nm.

5. The encapsulated resveratrol (RSV) nanoparticles of claim 1, wherein the encapsulated resveratrol (RSV) nanoparticles have a polydispersity index (PDI) ranging from about 0.195 to about 0.225.

6. The encapsulated resveratrol (RSV) nanoparticles of claim 5, wherein the encapsulated resveratrol (RSV) nanoparticles have a polydispersity index (PDI) of about 0.222.

7. The encapsulated resveratrol (RSV) nanoparticles of claim 1, wherein the encapsulated resveratrol (RSV) nanoparticles are spherical.

8. Encapsulated resveratrol (RSV) nanoparticles, consisting of:
a resveratrol core;
a gum arabic shell over the resveratrol core; and
a polyvinyl alcohol coating over the gum arabic shell, wherein a ratio of the RSV:gum arabic:polyvinyl alcohol (PVA) ratio in the encapsulated nanoparticles is about 1:5:5 (w/w/w).

9. The encapsulated resveratrol (RSV) nanoparticles of claim 8, wherein the encapsulated resveratrol (RSV) nanoparticles have an average size ranging from about 195 nm to about 210 nm.

10. The encapsulated resveratrol (RSV) nanoparticles of claim 8, wherein the encapsulated resveratrol (RSV) nanoparticles are spherical.

11. The encapsulated resveratrol (RSV) nanoparticles of claim 8, wherein the encapsulated resveratrol (RSV) nanoparticles have a polydispersity index (PDI) ranging from about 0.195 to about 0.225.

* * * * *